(12) United States Patent
Yadav (10) Patent No.: US 9,198,908 B2
(45) Date of Patent: Dec. 1, 2015

(54) METHODS FOR THE TREATMENT OF CARDIOVASCULAR CONDITIONS

(71) Applicant: ST. JUDE MEDICAL LUXEMBOURG HOLDINGS II S.A.R.L. ("SJM LUX II"), Luxembourg (LU)

(72) Inventor: Jay Yadav, Atlanta, GA (US)

(73) Assignee: ST. JUDE MEDICAL LUXEMBOURG HOLDINGS II S.A.R.L. ("SJM LUX II"), Luxembourg (LU)

(*) Notice: Subject to any disclaimer, the term of this patent is extended or adjusted under 35 U.S.C. 154(b) by 0 days.

(21) Appl. No.: 14/216,582

(22) Filed: Mar. 17, 2014

(65) Prior Publication Data
US 2014/0288085 A1    Sep. 25, 2014

Related U.S. Application Data

(60) Provisional application No. 61/786,766, filed on Mar. 15, 2013.

(51) Int. Cl.
| A61K 31/495 | (2006.01) |
| A61K 31/4985 | (2006.01) |
| A61K 31/519 | (2006.01) |
| A61B 5/00 | (2006.01) |
| A61B 5/0215 | (2006.01) |

(52) U.S. Cl.
CPC ........... *A61K 31/4985* (2013.01); *A61B 5/0215* (2013.01); *A61B 5/4848* (2013.01); *A61K 31/519* (2013.01); *A61B 5/6876* (2013.01)

(58) Field of Classification Search
USPC ................................................. 514/250, 252
See application file for complete search history.

(56) References Cited

U.S. PATENT DOCUMENTS

| 5,368,040 | A | 11/1994 | Carney |
| 5,817,320 | A | 10/1998 | Stone |
| 6,033,670 | A | 3/2000 | Bublot et al. |
| 6,153,199 | A | 11/2000 | Audonnet et al. |
| 6,277,078 | B1 | 8/2001 | Porat et al. |
| 6,705,990 | B1 | 3/2004 | Gallant et al. |
| 6,970,742 | B2 | 11/2005 | Mann et al. |
| 7,024,244 | B2 | 4/2006 | Muhlenberg et al. |
| 7,367,951 | B2 | 5/2008 | Bennett et al. |
| 7,481,771 | B2 | 1/2009 | Fonseca et al. |
| 7,569,572 | B2 * | 8/2009 | Bell et al. .................... 514/262.1 |
| 7,594,889 | B2 | 9/2009 | St. Ores et al. |
| 7,615,010 | B1 | 11/2009 | Najafi et al. |
| 7,646,901 | B2 | 1/2010 | Murphy et al. |
| 7,679,355 | B2 | 3/2010 | Allen et al. |
| 7,699,059 | B2 | 4/2010 | Fonseca et al. |
| 7,949,394 | B2 | 5/2011 | Salo et al. |
| 8,026,729 | B2 | 9/2011 | Kroh et al. |
| 8,127,618 | B1 | 3/2012 | Zhao et al. |
| 8,147,415 | B2 | 4/2012 | Liao et al. |
| 8,147,416 | B2 | 4/2012 | Fayram et al. |
| 8,231,539 | B2 | 7/2012 | Bardy |
| 8,273,031 | B2 | 9/2012 | Cohen et al. |
| 8,278,941 | B2 | 10/2012 | Kroh et al. |
| 8,301,252 | B2 | 10/2012 | Hatlestad et al. |
| 8,303,511 | B2 | 11/2012 | Eigler et al. |
| 8,545,436 | B2 | 10/2013 | Robertson et al. |
| 8,665,086 | B2 | 3/2014 | Miller et al. |
| 2002/0032384 | A1 | 3/2002 | Raymond et al. |
| 2003/0036683 | A1 | 2/2003 | Kehr et al. |
| 2005/0015014 | A1 | 1/2005 | Fonseca et al. |
| 2006/0047205 | A1 | 3/2006 | Ludomirsky et al. |
| 2006/0281681 | A1 | 12/2006 | Pilon |
| 2007/0043591 | A1 | 2/2007 | Meretei et al. |
| 2007/0088221 | A1 | 4/2007 | Stahmann |
| 2007/0250121 | A1 | 10/2007 | Miesel et al. |
| 2007/0282210 | A1 | 12/2007 | Stern |
| 2008/0077375 | A1 | 3/2008 | Fernandez |
| 2008/0077440 | A1 | 3/2008 | Doron |
| 2008/0243007 | A1 | 10/2008 | Liao et al. |
| 2008/0243016 | A1 | 10/2008 | Liao et al. |
| 2008/0300650 | A1 | 12/2008 | Gerber et al. |
| 2009/0006061 | A1 | 1/2009 | Thukral et al. |
| 2009/0030291 | A1 | 1/2009 | O'Brien et al. |
| 2009/0054793 | A1 | 2/2009 | Nunez et al. |
| 2009/0062313 | A1 * | 3/2009 | Kass et al. .................. 514/262.1 |
| 2009/0177106 | A1 | 7/2009 | Ricke et al. |
| 2009/0197922 | A1 | 8/2009 | Maitland et al. |
| 2009/0239883 | A1 | 9/2009 | Butrous et al. |
| 2009/0320836 | A1 | 12/2009 | Baker, Jr. |
| 2010/0056931 | A1 | 3/2010 | Soffer et al. |

(Continued)

FOREIGN PATENT DOCUMENTS

| WO | 2006/023603 | 3/2006 |
| WO | 2012/019191 | 2/2012 |

(Continued)

OTHER PUBLICATIONS

Frantz et al. "Continuous Hemodynamic Monitoring in Patients with pulmonary Arterial Hypertension." *The Journal of Heart and Lung Transplantation*. 2008, 27(7), 780-788.
Frantz, RP. "Hemodynamic monitoring in pulmonary arterial hypertension." *Expert Rev. Resp. Med*. 2011, 5(2), 173-178.
Fruhwald et al."Continuous Hemodynamic Monitoring in Pulmonary Hypertensive Patients Treated with Inhaled Iloprost." *Chest*. 2003, 124, 351-359.
Grignola et al. "Hemodynamic assessment of pulmonary hypertension". *World Journal of Cardiology*. 2011, 3(1), 10-17.
Guazzi et al. "Pulmonary hypertension due to left heart disease." *Circulation*. 2012, 126(8), 975-990.
International Search Report and Written Opinion, dated Aug. 8, 2014, issued in International Application No. PCT/US2014/030521, 15 pages.

(Continued)

*Primary Examiner* — Rei-Tsang Shiao (57) ABSTRACT

Provided herein are methods and systems for the treatment of cardiovascular conditions, including pulmonary hypertension (PH), in subjects that are being treated with a treatment regimen that includes a phosphodiesterase-5 (PDE-5) inhibitor.

24 Claims, 4 Drawing Sheets

(56) References Cited

U.S. PATENT DOCUMENTS

| | | | |
|---|---|---|---|
| 2010/0094144 | A1 | 4/2010 | Doron |
| 2010/0286535 | A1 | 11/2010 | Blomqvist |
| 2010/0305414 | A1 | 12/2010 | Koo et al. |
| 2011/0003610 | A1 | 1/2011 | Key et al. |
| 2011/0098767 | A1 | 4/2011 | Sugimachi et al. |
| 2011/0106200 | A1 | 5/2011 | Ziegler |
| 2011/0125023 | A1 | 5/2011 | Palti et al. |
| 2011/0144967 | A1 | 6/2011 | Adirovich |
| 2011/0201949 | A1 | 8/2011 | Bodecker et al. |
| 2011/0273287 | A1 | 11/2011 | Lalonde et al. |
| 2012/0004188 | A1 | 1/2012 | Belardinelli |
| 2012/0064006 | A1 | 3/2012 | Yadav |
| 2012/0065165 | A1 | 3/2012 | Aspland et al. |
| 2012/0071735 | A1 | 3/2012 | Caylor, III et al. |
| 2012/0100155 | A1 | 4/2012 | Stoloff et al. |
| 2012/0101430 | A1 | 4/2012 | Robertson et al. |
| 2012/0136583 | A1 | 5/2012 | Lazar et al. |
| 2013/0044704 | A1 | 2/2013 | Pang et al. |
| 2013/0204147 | A1 | 8/2013 | Blomqvist et al. |
| 2013/0224306 | A1* | 8/2013 | Gillies et al. ............ 424/613 |
| 2013/0245469 | A1 | 9/2013 | Yadav et al. |
| 2014/0155769 | A1 | 6/2014 | White et al. |
| 2014/0275861 | A1 | 9/2014 | Kroh et al. |
| 2015/0133796 | A1 | 5/2015 | Yadav |

FOREIGN PATENT DOCUMENTS

| | | |
|---|---|---|
| WO | 2013/142387 | 9/2013 |
| WO | 2014/081958 | 5/2014 |
| WO | 2014/145531 | 9/2014 |

OTHER PUBLICATIONS

Fuchs, W., et al., "In Vitro and In Vivo Relevance of Infectious Laryngotracheitis Virus gJ Proteins That Are Expressed from Spliced and Nonspliced mRNAs," Journal of Virology, vol. 79, No. 2, 2005, pp. 705-716.

Naeije, R., "Pulmonary Hypertension and Right Heart Failure in Chronic Obstructive Pulmonary Disease," Proceedings of the American Thoracic Society, vol. 2, 2005, pp. 20-22.

Johnson, D., et al., "Protection Against Infectious Laryngotracheitis by In Ovo Vaccination with Commercially Available Viral Vector Recombinant Vaccines," Avian Diseases, vol. 54, No. 4, 2010, pp. 1251-1259.

Mundt, A., et al., "Glycoprotein J of infectious laryngotracheitis virus is required for efficient egress of infectious virions from cells," Journal of General Virology, vol. 92, 2011, pp. 2586-2589.

Spatz, S.J., et al., "Comparative full genome analysis of four infectious laryngotracheitis virus (*Gallid herpesvirus*-1) virulent isolates from the United States," Virus Genes, vol. 44, 2012, pp. 273-285.

Weitzenblum, E., "Chronic Cor Pulmonale," Heart, vol. 89, No. 2, 2003, pp. 225-230.

International Preliminary Report on Patentability and Written Opinion, dated Feb. 12, 2013, received in connection with International Patent Application No. PCT/US2011/046953.

International Search Report, dated Feb. 29, 2012, received in connection with International Patent Application No. PCT/US2011/046953.

International Preliminary Report on Patentability and Written Opinion, dated Sep. 23, 2014, received in connection with International Patent Application No. PCT/US2013/032642.

International Search Report, dated Jul. 19, 2013, received in connection with International Patent Application No. PCT/US2013/032642.

International Preliminary Report on Patentability and Written Opinion, dated May 26, 2015, received in connection with International Patent Application No. PCT/US2013/071294.

International Search Report, dated Feb. 7, 2014, received in connection with International Patent Application No. PCT/US2013/071294.

International Search Report and Written Opinion, dated Apr. 13, 2015, received in connection with International Patent Application No. PCT/US2014/030322.

U.S. Appl. No. 14/534,834, filed Nov. 6, 2014.
U.S. Appl. No. 13/843,553, filed Mar. 15, 2013.
U.S. Appl. No. 14/086,478, filed Nov. 21, 2013.
U.S Appl. No. 14/215,818, filed Mar. 17, 2014.
U.S Appl. No. 13/205,459, filed Aug. 8, 2011.

Non-final Office Action, dated Jul. 2, 2015, received in connection with U.S. Appl. No. 13/843,553.

Non-Final Office Action, dated Aug. 6, 2014, received in connection with U.S. Appl. No. 13/205,459.

Final Office Action, dated May 1, 2014, received in connection with U.S. Appl. No. 13/205,459.

Non- Final Office Action, dated Aug. 6, 2013, received in connection with U.S. Appl. No. 13/205,459.

\* cited by examiner

METHODS FOR THE TREATMENT OF CARDIOVASCULAR CONDITIONS

CROSS REFERENCE TO RELATED APPLICATIONS

This application claims benefit of U.S. Provisional Application No. 61/786,766, filed Mar. 15, 2013, which is hereby incorporated by reference in its entirety.

FIELD OF THE INVENTION

This application generally relates to devices, systems, and methods for the treatment of cardiovascular conditions.

BACKGROUND OF THE INVENTION

Hearts exposed to sustained hemodynamic overload undergo molecular, cellular, muscular, and chamber morphologic changes that are typically maladaptive and contribute to progressive cardiac dysfunction and ultimately heart failure. Pathophysiological stimuli that trigger such responses include hypertension, valvular disease, neurohormonal stress, and excessive chamber filling associated with a decline in pump function. These trigger alterations in multiple cellular signaling and transcription pathways that induce muscle cell growth, worsened function of the heart muscle, hypertrophic remodeling and cardiac dilation.

Enlargement of the heart is a chronic and progressive condition that ultimately results in heart failure. Heart failure affects over 5 million Americans, with more than 500,000 new diagnoses annually in the United States alone. Heart failure remains the leading cause of death in the United States. Improved methods for the treatment of cardiovascular conditions, such as pulmonary hypertension and cardiac hypertrophy, are urgently required.

SUMMARY OF THE INVENTION

Provided herein are methods and systems for the treatment of cardiovascular conditions, including pulmonary hypertension (PH), in subjects that are being treated with a phosphodiesterase-5 (PDE-5) inhibitor.

For example, provided are methods of evaluating the progression or improvement of a cardiovascular condition in a subject being administered a treatment regimen that includes a PDE-5 inhibitor, or predicting an outcome in a subject being administered a treatment regimen that includes PDE-5 inhibitor. Methods can include obtaining one or more pulmonary arterial (PA) hemodynamic readings comprising a PA hemodynamic waveform from the subject using an implantable pressure sensor, processing the PA hemodynamic waveform to obtain a cardiovascular parameter, and comparing the cardiovascular parameter obtained from the subject to a standard to determine or predict the progression of the cardiovascular condition, the improvement of the cardiovascular condition, the outcome of the cardiovascular condition, or a combination thereof.

Once obtained, this information can be used, for example by a clinician, to direct treatment of the subject's cardiovascular condition. For example, methods can further include maintaining the treatment regimen administered to the subject when the comparison indicates or predicts efficacy of the treatment regimen for the treatment of the cardiovascular condition in the subject, or altering the treatment regimen administered to the subject when the comparison indicates or predicts substandard efficacy of the treatment regimen for the treatment of the cardiovascular condition in the subject (e.g., worsening of the cardiovascular condition, or no improvement in the cardiovascular condition).

The methods described herein can employ any suitable cardiovascular parameter. In some embodiments, the cardiovascular parameter can be selected from the group consisting of pulmonary arterial pressure (PAP), cardiac output (CO), peripheral vascular resistance (PVR), total peripheral resistance (TPR), and combinations thereof. The standard can comprise one or more cardiovascular parameters previously determined from the subject (e.g., a trend in a subject's cardiovascular parameter over time), a clinically relevant target cardiovascular parameter for the subject, or a composite of cardiovascular parameters previously determined from a plurality of subjects (e.g., average values previously obtained from a population of patients sharing one or more subject characteristics with the subject).

Also provided are systems for practicing the methods described herein, including systems for evaluating the progression or improvement of cardiovascular condition in a subject being administered a treatment regimen that includes a PDE-5 inhibitor, or predicting an outcome in a subject being administered a treatment regimen that includes PDE-5 inhibitor. Example systems can comprise an implantable pressure sensor (e.g., a pressure sensor implanted in the pulmonary artery of a subject) configured to obtain a pulmonary artery pressure waveform; a processor; and a memory operably coupled to the processor. The memory can include computer-executable instructions stored thereon that, when executed by the processor, cause the processor to receive the one or more PA hemodynamic readings obtained from the implantable pressure sensor; process the PA hemodynamic waveform to obtain a cardiovascular parameter; compare the cardiovascular parameter to a standard; and provide an output based on the comparison of the cardiovascular parameter to the standard.

Example outputs can include indicators or predictors of improvement or worsening of the cardiovascular condition in the subject (e.g., probabilities, scores, subject status indicators, trend values for cardiovascular parameters such as PAP, CO, PVR and/or TPR, graphs plotting values for PAP, CO, PVR and/or TPR, etc.), instructions for treatment (e.g., instructions or indicators to maintain the treatment regimen that includes a PDE-5 inhibitor, instructions to alter the treatment regimen, such as instructions to modify the administration protocol of the PDE-5 inhibitor, instructions to discontinue use of the PDE-5 inhibitor, instructions to administer an alternative therapeutic agent or regimen, etc.) or combinations thereof.

The details of one or more embodiments are set forth in the accompanying drawings and the description below. Other features, objects, and advantages will be apparent from the description and drawings, and from the claims.

DETAILED DESCRIPTION

Provided herein are methods for monitoring, assessing, treating, and for developing treatments for cardiovascular conditions, including pulmonary hypertension (PH), particularly in subjects being administered (i.e., undergoing treatment with) a treatment regimen that includes a phosphodiesterase-5 (PDE-5) inhibitor.

PDE-5 (phosphodiesterase type 5) inhibitors block the degradative action of PDE-5 on cyclic GMP in the smooth muscle cells lining the arterial walls of the lungs. The subject can be undergoing treatment with a treatment regimen that includes any suitable PDE-5 inhibitor. PDE-5 inhibitors are known in the art, and include, for example, avanafil, lodenafil, mirodenafil, sildenafil, tadalafil, vardenafil, udenafil, zaprinast, and icariin. For example, in some embodiments, the subject is being treated with a PDE-5 inhibitor selected from the group consisting of sildenafil (e.g., sildenafil citrate, commercially available under the trade name VIAGRA®), tadalafil (commercially available under the trade name CIALIS®), vardenafil (commercially available under the trade name LEVITRA®), or combinations.

In some embodiments, the cardiovascular condition can comprise PH. PH is a broad clinical term used to describe pulmonary conditions which involve an increase in blood pressure in the lung vasculature (i.e., the pulmonary artery, the pulmonary vein, or the pulmonary capillaries). The increase in blood pressure leads to shortness of breath, dizziness, fainting, and other symptoms, all of which are exacerbated by exertion. Eventually, PH can lead to chronic hypoxia, heart failure, and death. According to current clinical classification, PH is divided into five different categories based on pathophysiological mechanisms, clinical presentation, and therapeutic methods. See Simonneau, et al. J. Am. Coll. Cardio. 43(12) Suppl. S: 5S-12S (2004). The five different types of PH include (1) PH associated with pulmonary arterial hypertension (PAH); (2) PH associated with left heart disease (LHD) (i.e., pulmonary venous hypertension); (3) PH associated with lung diseases and/or hypoxemia (4) PH due to chronic thrombotic and/or embolic disease; and (5) miscellaneous pulmonary hypertension. In certain embodiments, the cardiovascular condition can comprise PH associated with LHD. In certain embodiments, the cardiovascular condition can comprise PH associated with right heart disease.

Methods can involve obtaining one or more pulmonary arterial (PA) hemodynamic readings comprising a PA hemodynamic waveform from the subject using an implantable pressure sensor, and processing the PA hemodynamic waveform to obtain a cardiovascular parameter. Once obtained, the cardiovascular parameter can be used to assess, treat, and/or develop new treatments for the subject. For example, the cardiovascular parameter obtained from the subject can be compared to a standard. The methods can optionally be used to evaluate the progress of the cardiovascular condition in the subject, to predict an outcome in the subject, to treat the subject, or to develop a therapeutic regimen.

The method can include determining one or more cardiovascular parameters from subject. Examples of suitable cardiovascular parameters include pulmonary arterial pressure (PAP), cardiac output (CO), peripheral vascular resistance (PVR), total peripheral resistance (TPR), heart rate, respiratory rate, dicrotic notch information, and combinations thereof. In some embodiments, the cardiovascular parameter can be selected from the group consisting of PAP, CO, PVR, TPR, and combinations thereof. Other cardiovascular physiological information can also be utilized in conjunction with the methods described herein, including combinations of mechanical and chemical cardiovascular parameters, such as pulse oximetry or blood oxygenation.

Once determined from the subject, cardiovascular parameters can be compared to a standard. In some cases, the standard can include one or more cardiovascular readings/parameters previously determined from the same subject. For example, the standard can optionally include a cardiovascular parameter derived from a PA hemodynamic waveform obtained from the subject using an implantable pressure sensor. In certain embodiments, the standard can include a plurality of cardiovascular parameters previously determined from the subject. In this way, trends in one or more cardiovascular parameters (e.g., PAP, CO, PVR, and/or TPR) in the subject can be monitored. These trends can optionally be used to monitor the progression or outcome of the cardiovascular condition in the subject. These trends can optionally be used to assess the efficacy of the PDE-5 treatment regimen currently being administered to the subject.

For example, lowering or increased trend in certain cardiovascular parameters, over time, in the subject can indicated improvement in the condition of a subject being treated with a PDE-5 inhibitor. In the case of a subject afflicted with a cardiovascular condition, such as PH associated with LHD, a lowering trend in PVR, PAP, or TPR, and/or a increased trend in CO, over time in a subject can indicate or predict improvement in the cardiovascular condition, indicate efficacy of the PDE-5 treatment regimen for the cardiovascular condition, or a combination thereof. This can also optionally indicate improved outcome in the subject, such as, for example, reduced hospitalizations, lower mortality, or lower morbidity.

Conversely, an increased trend in PVR, PAP, or TPR, or a lowering trend in CO, over time, can indicate or predict progression of the cardiovascular condition in the subject, predict worsening of the cardiovascular condition in the subject, indicate suboptimal efficacy of the PDE-5 treatment regimen for the cardiovascular condition, or a combination thereof. This can also optionally indicate a potentially negative outcome in the subject, such as, for example, increased hospitalizations, increased mortality, or increased morbidity. Optionally, the predicted outcome is mortality rate, wherein the mortality rate is either reduced or increased for the subject.

By way of an example, if PAP is increased compared to a standard, the mortality rate can be expected to be increased. By way of another example, if the PAP is decreased compared to a standard, the mortality rate can be expected to be decreased. Optionally, the predicated outcome is hospitalization rate, wherein the hospitalization rate is either reduced or increased for the subject. By way of an example, if PAP is increased compared to a standard, the hospitalization rate for the subject can be expected to be increased. By way of another example, if PAP is decreased as compared to a control, the hospitalization rate for the subject can be expected to be decreased. A reduced expected hospitalization rate can result from, for example, a reduction in hospitalizations for heart failure.

In some cases, the standard can include one or more cardiovascular readings/parameters previously determined from one or more different subjects. In some embodiments, the standard can include a composite of one or more cardiovascular readings/parameters previously determined from a plurality of subjects (e.g., a population of subjects afflicted with the same cardiovascular condition as the subject). In some cases, the one or more cardiovascular readings/parameters previously determined from a plurality of subjects include cardiovascular parameters derived from PA hemodynamic waveforms obtained from the subjects using implantable pressure sensors.

In some embodiments, the standard may be provided in a database of stored cardiovascular physiological information. Information on the database can comprise one or more cardiovascular readings/parameters previously determined from a plurality of subjects correlated with at least one of patient profile and demographic information (age, race, gender, weight, and the like), medical history, medications, classifications, diagnoses, and the like. Other information can comprise at least one of patient episodes, such as surgeries, catheterizations, changes in weight or medication that are associated with a timestamp at entry, and the like. The described methods can further comprise determining one or more characteristics of the subject (termed "subject characteristics"). The subject characteristics can be a physical, physiologic, metabolic, chronological, disease state, drug administration history, medical history, or genetic characteristic. Methods can further involve accessing the database of stored cardiovascular physiological information, querying the database to identify one or more cardiovascular readings/parameters previously determined from a plurality of subjects sharing one or more subject characteristics with the subject, selecting one or more cardiovascular readings/parameters previously determined from a plurality of subjects sharing one or more subject characteristics with the subject, and deriving a composite of these cardiovascular readings/parameters (e.g., an average of these cardiovascular readings/parameters) that can be compared with the one or more cardiovascular parameters obtained from the subject.

In some cases, the standard can also optionally be a clinically relevant target value for a cardiovascular parameter for the subject. For example, an optional clinical target standard is a PAP of about 25 mmHg. A clinically relevant target value can be a value that is a normal value for the subject, or a population of which the subject is a member, or an improved value for the subject, goal value for the subject, or any other value determined by a health care professional managing the subject. Optionally, the clinically relevant target for the cardiovascular parameter can be, for example, determined by a health care professional treating or managing the subject.

Thus, trends in one or more cardiovascular parameters (e.g., PAP, CO, PVR, and/or TPR) in the subject can be monitored relative to previous values from the subject, composite values obtained from a population of analogous patients, or to clinical target values that may optionally be determined by a health care professional treating or managing the subject. This can be done to evaluate the progress of the cardiovascular condition in the subject, to predict an outcome in the subject, to treat the subject, or to develop a therapeutic regimen (e.g., for treating the subject, or for treating other subjects having similar subject characteristics).

The trends can be used to determine if the subject is improving. For example, a decrease in the one or more PAP values compared to the standard PAP value, combined with one or more increased or stable CO estimates compared to the standard CO value can indicate or predict improvement of the cardiovascular condition in the subject. In another example, one or more stable PAP values compared to the standard PAP value, combined with one or more increased CO estimates compared to the CO standard value indicates or predicts improvement of the cardiovascular condition in the subject.

Alternatively, a decrease in one or more CO estimates compared to the standard CO value, combined with one or more increased or stable PAP values compared to the standard PAP value can indicate or predict worsening of the cardiovascular condition in the subject. In another example, an increase in one or more PAP values compared to the standard PAP values, combined with a stable or decreased CO value compared to the standard CO value indicates or predicts worsening of the cardiovascular condition in the subject. Optionally, trends in PAP values and trends in CO value are used together to monitor progress or to predict outcome in a subjects being treated with PDE-5 inhibitors. Optionally, trends in PAP values and trends in CO value are used together to assess the efficacy of a treatment regimen that includes a PDE-5 inhibitors for the treatment of a cardiovascular condition, such as PH (e.g., PH associated with LHD).

In other examples, PAP value trends or CO value trends are used independently to monitor progress or to predict outcomes in subjects being treated with PDE-5 inhibitors, and/or are used independently to assess the efficacy of a treatment regimen that includes a PDE-5 inhibitors for the treatment of a cardiovascular condition, such as PH (e.g., PH associated with LHD). By extension, other cardiovascular parameters (e.g., PVR, and/or TPR values) can similarly be employed in the methods described above.

In certain embodiments, trends in one or more cardiovascular parameters (e.g., PAP, CO, PVR, and/or TPR) in the subject can be monitored relative to previous values from the subject, composite values obtained from a population of analogous patients, or to clinical target values that may optionally be determined by a health care professional treating or managing the subject to assess the efficacy of a treatment regimen that includes a PDE-5 inhibitors for the treatment of a cardiovascular condition, such as PH (e.g., PH associated with LHD).

Example methods can include administering to a subject having a cardiovascular condition a treatment regimen that includes a PDE-5 inhibitor; obtaining one or more pulmonary arterial (PA) hemodynamic readings comprising a PA hemodynamic waveform from the subject using an implantable pressure sensor; and processing the PA hemodynamic waveform to obtain a cardiovascular parameter (e.g., PAP, CO, PVR, and/or TPR). Once obtained, the cardiovascular parameter can be compared to a standard to assess the efficacy of the treatment regimen, or to develop a treatment regimen (e.g., for treating the subject, or for treating other subjects having similar subject characteristics).

By way of example, comparison of a PAP value can used to monitor the effect of the administered treatment regimen that includes a PDE-5 inhibitor on the cardiovascular condition in the subject. A decrease in the one or more determined PAP values compared to a standard, for example a decreasing trend in the subject's PAP values, indicates a beneficial effect of the administered treatment regimen on the cardiovascular condition in the subject. An increase in the one or more determined PAP values compared to a standard, for example an increasing trend in the subject's PAP values, indicates no beneficial effect of the administered treatment regimen on the cardiovascular condition in the subject.

In the case of CO, an example method for evaluating the effect of a treatment regimen that includes a PDE-5 inhibitor on a subject having a cardiovascular condition can include administering a treatment regimen that includes a PDE-5 inhibitor to the subject and obtaining a pulmonary artery pressure waveform from the subject. Cardiac output (CO) can then be estimated using the pulmonary artery pressure waveform and compared to a standard value. The comparison of a CO can used to monitor the effect of the administered treatment regimen that includes a PDE-5 inhibitor on the cardiovascular condition in the subject. For example, an increase in the one or more estimated CO values compared to a standard, for example an increasing trend in the subject's CO estimates, indicates a beneficial effect of the administered treatment regimen on the cardiovascular condition in the subject. A decrease in the one or more estimated CO values compared to a standard, for example a decreasing trend in the subject's CO estimated values, indicates no beneficial effect of the administered treatment regimen on the cardiovascular condition in the subject.

Multiple cardiovascular parameters can be evaluated in combinations. For example, the comparisons of PAP and CO to standard, for example trends in both PAP and CO, can used to assess the efficacy of a treatment regimen that includes a PDE-5 inhibitors for the treatment of a cardiovascular condition, such as PH (e.g., PH associated with LHD).

The trends can be used to determine the effect of the administered treatment regimen on the cardiovascular condition in the subject (e.g., PH associated with LHD). For example, a decrease in the one or more PAP values compared to the standard, combined with one or more increased or stable CO estimates compared to the standard can indicates a beneficial effect of the administered treatment regimen on the cardiovascular condition in the subject. In another example, one or more stable PAP values compared to the standard, combined with one or more increased CO estimates compared to s standard indicates a beneficial effect of the administered treatment regimen on the cardiovascular condition in the subject.

Alternatively, a decrease in one or more CO estimates compared to the standard, combined with one or more increased or stable PAP values compared to the standard can indicate no effect or a detrimental effect of the administered treatment regimen on the cardiovascular condition in the subject. In another example, an increase in one or more PAP values compared to the standard, combined with a stable or decreased CO value compared to the standard indicates no effect or a detrimental effect of the administered treatment regimen on the cardiovascular condition in the subject.

By extension, other cardiovascular parameters (e.g., PVR, and/or TPR values) can similarly be employed in the methods described above.

The administration of the treatment regimen that includes a PDE-5 inhibitor, for example, the PDE-5 inhibitor administered, dosage, timing, protocol, or the like, can be modified or maintained after determining the effect of the treatment regimen of the cardiovascular condition in the subject. For example, administration of the treatment regimen is optionally maintained at its current dosage and or dosing regimen when improvement is indicated. In another example, the treatment regimen is changed, or the dosage or dosing regimen modified when improvement is not indicated. In another example, the information obtained on PAP, CO, or both are used to determine an effective dosage or administration protocol for a PDE-5 inhibitor or to evaluate the same, for example, in a clinical trial setting.

Therapeutic goals for the treatment of a cardiovascular condition, such as PH (e.g., PH associated with LHD), can optionally include lowering or maintaining PAP and/or increasing or maintaining CO. Additional therapeutic goals include reducing or maintaining PVR and/or reducing or maintaining TVR. Optionally CO is increased while PAP is reduced in the subject. Optionally, CO or PAP is increased while PAP or CO is maintained respectfully.

In some embodiments, the method includes altering the treatment regimen administered to the subject. Altering the treatment regimen administered to the subject can include, but is not limited to, administering less of the PDE-5 inhibitor, administering more of the PDE-5 inhibitor, administering an alternative PDE-5 inhibitor, discontinuing the use of the PDE-5 inhibitor, altering the timing of administration of the PDE-5 inhibitor, administering one or more additional therapeutic agents or regimens, or combinations thereof.

In some embodiments, altering the treatment regimen administered to the subject can include administering one or more additional therapeutic agents or regimens. In some embodiments, methods described herein can involve identifying a candidate therapeutic agent for administration to the subject. In some embodiments, information regarding one or more candidate therapeutic agents or regimens may be provided in a database, such as the database described above. In certain embodiments, the one or more candidate therapeutic agents or regimens can be correlated with one or more subject characteristics, one or more cardiovascular parameters, one or more predicted effects of the candidate therapeutic agents or regimens, or a combination thereof. Methods of identifying a candidate therapeutic can further comprise determining one or more subject characteristics, accessing the database described above, querying the database to identify one or more candidate therapeutic agents or regimens based on one or more subject characteristics of the subject being treated, one or more cardiovascular parameters, and/or one or more predicted effects of the candidate therapeutic agent or regimen (e.g., a desired treatment outcome or clinical endpoint).

The methods can optionally be used to develop a therapeutic regimen for a cardiovascular conditions, including PH, particularly PH associated with LHD. The term "develop" or "developing" or "development" as used herein in reference to therapeutics are broad terms that include, by way of example and not limitation, prospective design, or selection, of one or more potential therapeutic methods or compounds, or retrospective study of one or more therapeutic methods or compounds or design of studies of such therapeutic methods or compounds. In this regard, to develop or development of a therapeutic can include, for example, changes to an active ingredient or formulation and also includes, for example, study design for a therapeutic. Optionally, study design is for a clinical trial and development of a study design can include establishing trial metrics or trial durations.

Optionally, the therapeutic agent can be modified to increase the indicated effect. For example, if the indicated effect is desired (e.g., therapeutic efficacy for PH is observed), the structure of the therapeutic agent can be modified to increase the indicated effect. The therapeutic agent can also be modified to decrease the indicated effect. For example, if the indicated effect is not desirable, then the structure of the therapeutic agent can be modified to decrease the indicated effect. Moreover, an administration characteristic of the therapeutic agent can be modified to increase or decrease the indicated effect. The administration characteristic can be selected from the group consisting of dosage amount, number of doses, timing of doses, route of administration, and total dosage. When the indicated effect is to be increased or decreased, one or more portions of the therapeutic agent responsible for the indicated effect can be determined. Optionally, a second therapeutic agent including the one or more portions of the therapeutic agent responsible for the indicated effect can be designed. In some embodiments, the method includes altering the PDE-5 inhibitor administered to the subject or optimizing the dose of the PDE-5 inhibitor administered to the subject to treat PH, particularly PH associated with LHD.

Sensors

In the described methods, the cardiovascular physiological readings are optionally obtained with a wireless sensor implanted in the subject. Optionally, the implanted sensor is a pressure sensor, which is optionally implanted in the pulmonary artery of the subject. Optionally, the sensor lacks percutaneous connections. Optionally, the sensor is energized from an external source. Optionally, the sensor is a passive sensor energized to return pressure readings by an electromagnetic field.

An effective system and sensor for measurement of PA hemodynamic readings is the CARDIOMEMS (Atlanta, Ga.) heart sensor. As described by U.S. Pat. No. 7,699,059 entitled "Implantable Wireless Sensor" and U.S. Pat. No. 7,679,355 entitled "Communicating with an Implanted Wireless Sensor," these sensors are MEMS-based sensors that are implanted in the pulmonary artery, more particularly in the distal pulmonary artery branch and are configured to be energized with RF energy to return high-frequency, high-fidelity dynamic pressure information from a precisely-selected location within a patient's body. Because of the nature of the sensors described above, the PA pressure waveform is optionally obtained outside of a typical clinical evaluation environment. For example, the CARDIOMEMS sensor can provide ambulatory measurements of hemodynamic parameters, such as PAP, outside of a traditional hospital setting. "Ambulatory measurements" refers to measurements that are made in normal daily-living situations where the patient is not bedridden in a clinical setting. For example, sleeping (e.g., for studies and therapies of sleep apnea), eating and exercise activities at the home or work environments where RHC and other more invasive procedures are largely impractical and/or risky. Ambulatory measurements of cardiovascular physiological information can be more representative of living conditions of a patient who is suffering from a disease and/or undergoing treatment via a therapeutic regimen. The CARDIOMEMS sensor is non-invasive after implantation, facilitating ambulatory use. For example, in some embodiments, the PA waveform can optionally be obtained while the subject is exercising. Exercising can include any activity of the subject. For example, exercise or exercising can include activities of daily living, prescribed exercise, walking, biking, running or the like. Optionally, the PA pressure waveform is obtained while the subject is asleep.

In some embodiments, the cardiovascular physiological readings comprise a high fidelity, real-time PA pressure waveform which can be processed to obtain one or more desired cardiovascular parameters. Cardiovascular waveforms obtained with the CARDIOMEMS sensor are examples of "high fidelity" PA pressure waveforms.

Figure 4:
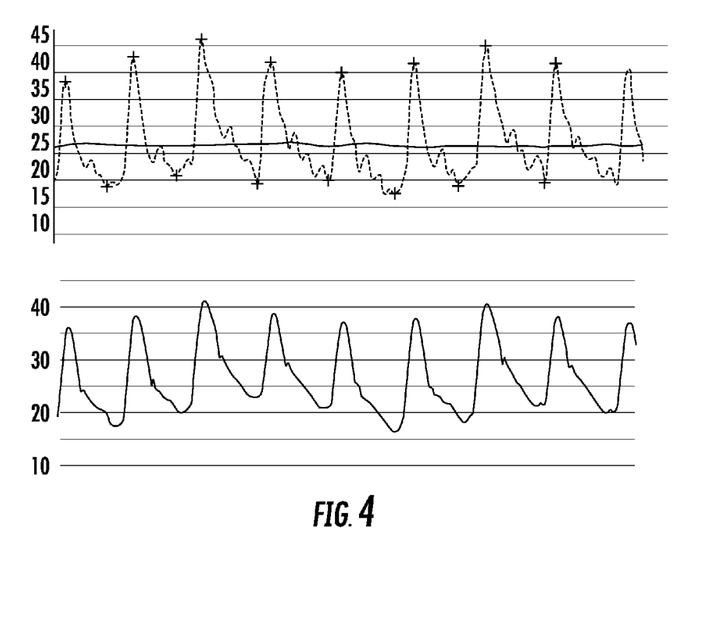
FIG. 4 shows comparison between the PA hemodynamic waveform obtained using right heart catheterization (top) and CARDIOMEMS implantable pressure sensor (bottom). The waveform obtained using RHC shows some undesired whip or overshoot that is believed to exceed actual systolic and diastolic pressures and which can lead to error and uncertainty. The CARDIOMEMS sensor waveform on the bottom, in contrast, exhibits high-fidelity through its smooth and undistorted waveform.
Figure 5:
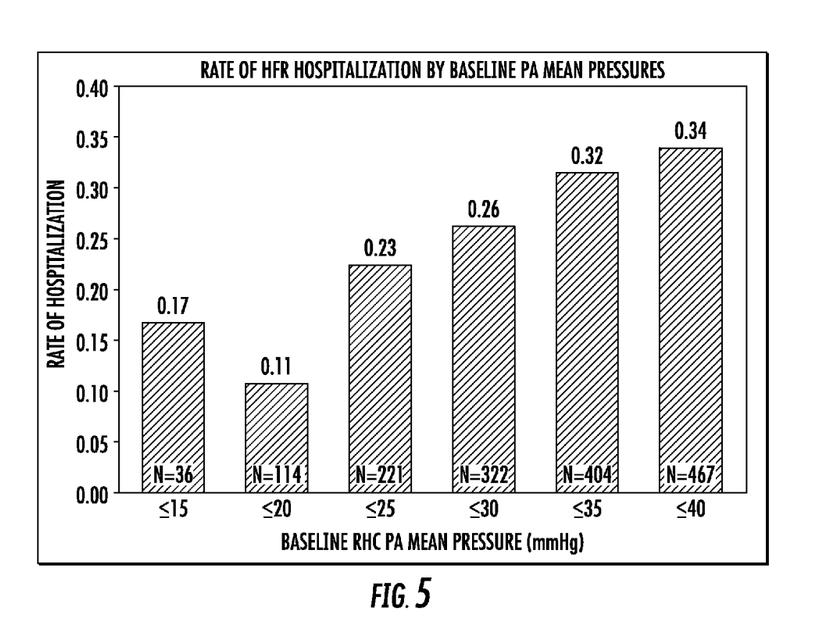
FIG. 5 is a graph showing rates of hospitalization by baseline PA mean pressures. This graph shows elevated hospitalization rates with elevated mean PAP.

As shown in FIG. 4, PA pressure waveforms measured using other methods, such as right heart catheterization (RHC; top waveform), exhibit undesired whip or overshoot that is believed to exceed systolic and diastolic pressures and which can lead to error and uncertainty. In contrast, the CARDIOMEMS sensor PA waveform (FIG. 4, bottom waveform) exhibits high fidelity through its smooth and undistorted waveform. For example, the dicrotic notch is clear and pronounced compared to the RHC gold standard.

The CARDIOMEMS pressure sensor allows for sampling rates of at least 2,000 samples per second without fluidic artifacts, and can be collected without line occlusion, which is the tendency of the line of a RHC to affect the hemodynamic measurements, and a lack of distortion due to movement that occurs in invasive procedures with long leads or wires extending from the patient. The accuracy of the CARDIOMEMS sensor data are also aided by the addition of resistance effects to the basic Bernoulli model, using Windkessel principles.

The high fidelity waveform is not subject to mechanical artifact with movement, which is commonly observed with conventional invasive blood pressure measurements, using a fluid-filled catheter. Further, the implanted sensor measures absolute pressure and the blood pressure waveform is determined by subtraction of atmospheric pressure, measured by the external measurement system. There is no need for external alignment and leveling of a reference transducer to perform measurements, as is required for conventional invasive blood pressure measurement with a fluid-filled catheter. These features make an implanted wireless sensor especially well-suited for measuring hemodynamic parameters without limitation to activity state or across changes in activity state.

Figure 6:
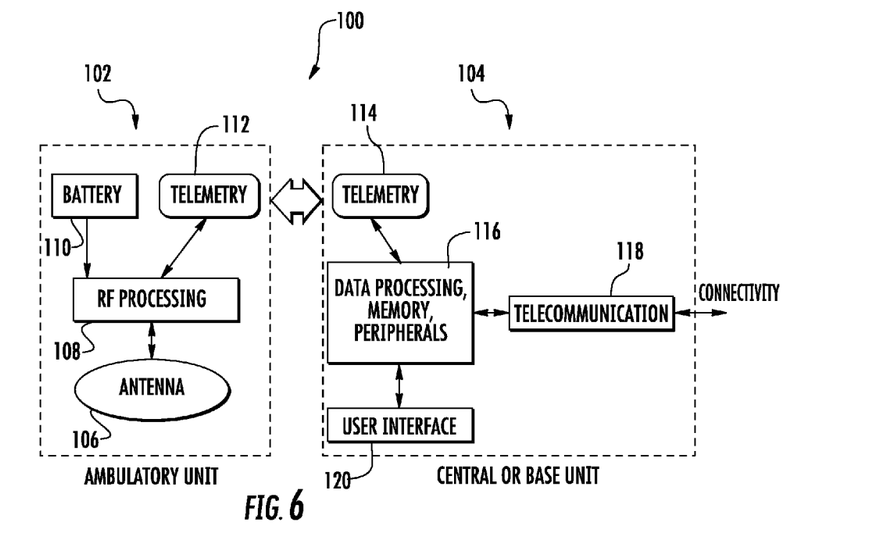
FIG. 6 is a block diagram of an embodiment of an ambulatory system which can be used in conjunction with the methods described herein.

In some embodiments, cardiovascular physiological readings are optionally obtained, for example during exercise, using an ambulatory system. Referring now to FIG. 6, an exemplary ambulatory system 100 is shown. The ambulatory system 100 can include an ambulatory unit 102 and a base unit 104. The ambulatory unit 102 and the base unit 104 can be communicatively connected through a communication link. This disclosure contemplates the communication link is any suitable communication link. For example, a communication link may be implemented by any medium that facilitates data exchange between the ambulatory unit 102 and the base unit 104 including, but not limited to, wired, wireless and optical links. Optionally, the communication link is a wireless link. For example, the ambulatory unit 102 and the base station 104 can be configured to communicate with each other using a wireless communication protocol such as WiFi, BLUETOOTH or ZIGBEE, for example. It should be understood that other standard or proprietary protocols can optionally be used by the ambulatory unit 102 and the base station 104.

The ambulatory unit 102 includes an antenna 106, an electronics unit 108 (e.g., RF processing unit), a power source 110 (e.g., battery) and a telemetry circuit 112. Optionally, as discussed above, the ambulatory unit 102 can be the external measurement system that is worn by the patient. The antenna 106 is configured to inductively couple energy to a sensor such as the implantable MEMS-based pressure sensor discussed above, for example, and receive return signals from the sensor. The return signals received at the ambulatory unit 102 via the antenna 106 can be processed by the electronics unit 108. For example, the electronics unit 108 can be configured to determine a pressure measurement from the signals as described in U.S. Pat. No. 7,679,355, entitled "Communicating with an Implanted Wireless Sensor." As discussed below, the processed signal can be transmitted the base unit 104 for storage and/or further processing. In its most basic configuration, the electronics unit 108 can include a processing unit and memory. The memory can optionally be volatile or non-volatile memory or some combination of the two. The processing unit can be configured to perform the arithmetic and logic operations necessary for operation of the ambulatory unit 102. For example, the processing unit can be configured to execute program code encoded in the memory.

Additionally, the power source 110 can provide power to the other components of the ambulatory unit such as antenna 106, the electronics unit 108 and the telemetry circuit 112. The telemetry circuit 112 allows the ambulatory unit 102 to communicate with other devices such as the base unit 102, for example, over the communication link. The telemetry circuit 112 can optionally include a transceiver and a microprocessor. Additionally, the transceiver and microprocessor can optionally be the same component. It should be understood that the ambulatory unit 102 discussed above is provided only as an example and that the ambulatory unit 102 can include more or less features than those discussed above.

The base unit 104 includes a telemetry circuit 114, a data processing circuit 116, a network connection 118 and a user interface 120. Optionally, the base unit 104 is a computing device such as desktop computer, laptop computer, tablet device, etc. The telemetry circuit 114 is similar to the telemetry circuit discussed above and is therefore not discuss in further detail below. In its most basic configuration, the data processing unit 116 can include a processing unit and memory. The memory can optionally be volatile or non-volatile memory or some combination of the two. The processing unit can be configured to perform the arithmetic and logic operations necessary for operation of the base unit 104. For example, the processing unit can be configured to execute program code encoded in the memory. Additionally, the network connection 118 allows the base unit 104 to communicate with other devices. For example, the base unit 104 can optionally be connected to a computer network such as a LAN, WAN, MAN, etc. via the network connection 118. Alternatively or additionally, the user interface 120 can include one or more input device (e.g., keyboard, touch screen, mouse, etc.) and/or output devices (e.g., display screen, speakers, printers, etc.). The above components are well known in the art and are therefore not discussed in further detail below. It should be understood that the base unit 104 discussed above is provided only as an example and that the base unit 104 can include more or less features than those discussed above.

Optionally, to allow effective monitoring of patients while active (e.g., during exercise), the ambulatory unit 102 can be designed to be worn on the patient's body. For example, harnessing methods can be used to fix the ambulatory unit 102 properly to the patient. In one example implementation, the electronics unit 108 and battery 110 can be contained within one or more pockets of a garment such as a vest, for example. The electronics unit 108 and the battery 110 can optionally be combined into a single housing or can optionally be housed separately. To provide for the adequate signal integrity, the antenna 106 can be positioned in a fixed position with respect to the sensor (e.g., the implanted MEMS-based sensor). Positioning of the antenna 106 can be flexible to provide for optimal coupling, and therefore, the means of fastening the antenna 106 can provide options for adjusting positioning. These options include movement of antenna 106 physically to another location and/or adjusting/tightening straps to move the relative location of a permanently fixed antenna 106 to a more optimal position. Optionally, the antenna 106 can be sewn in place within a garment such as a vest, or the antenna 106 can be fixed by some means of a temporary fabric fastener such as hook and loop (e.g., VELCRO). Optionally, in the PH applications, the antenna 106 can be fixed on the patient's back, for instance, over the patient's shoulder blade and can be communicatively connected to the electronics unit 108 with a cable. Alternatively, the antenna 106 can optionally communicate signals received by the antenna 106, for example, over a short range, directly to the base unit 104. In other words, the base unit 104 can be configured to determine a pressure measurement from the signals as discussed above. As discussed above, the ambulatory unit 102 can communicate with the base unit 104 over the communication link, which can be a wireless communication link, for example. The ambulatory unit 102 can optionally be worn by the patient who is located remotely from the base unit 104. The ambulatory unit 102 can communicate data including, but not limited to, data read from the sensors (e.g., the implanted MEMS-based sensors), diagnostic data from the ambulatory unit 102 and barometric pressure. The diagnostic data can include status information such battery status, temperature, etc. This disclosure contemplates that the base unit 104 can communicate with a plurality of ambulatory units at the same time. For example, a plurality of patients, each having an ambulatory unit, can be monitored at the same time. Transmission/reception of data between the base unit 104 and a plurality of ambulatory units can be synchronized to prevent interference. In one implementation, the base unit 104 can control synchronization. For example, each ambulatory unit 102 can be associated with a unique identifier, and the base unit 104 can poll a specific ambulatory unit using its unique identifier to initiate communication. In other words, the base unit 104 can be configured to send a message to an ambulatory unit, and the ambulatory unit can "wake up" and communicate with the base unit 104 upon receipt. Alternatively, the plurality of ambulatory units can control synchronization. For example, each of the ambulatory units can be configured to monitor communications between the other ambulatory units and the base unit 104. The base unit 104 can have a predetermined duty cycle for transmission and reception (e.g., a predetermined transmit-read cycle). The predetermined duty cycle can optionally be 10 microseconds. The base unit 104 can therefore be repeatedly available to receive communications at specified times. It should be understood that the predetermined duty cycle can be more or less than 10 microseconds. The plurality of ambulatory units can synchronize their respective wake periods (e.g., communication periods) into a predetermined order. Alternatively or additionally, the plurality of ambulatory units 102 can agree upon a synchronization order through a networking algorithm. This can optionally be achieved through direct communication from the base unit 104 (e.g., a star network) or through ambulatory unit to ambulatory unit communication in a repeater pattern (e.g., a mesh network).

Optionally, the ambulatory unit 102 can be configured to use one or more duty cycle sequences (e.g., ON/OFF, wake/sleep, etc.) to reduce power requirements. By reducing the power drawn by the ambulatory unit 102, the useful battery life can be extended. In other words, the ambulatory unit 102 can operate for a longer period of time without re-charging its power source 110. The ambulatory unit 102 can be configured to have a "wake" mode in which the ambulatory unit 102 is capable of communicating and/or is communicating with the base unit 104 and a "sleep" mode where its power requirements are reduced. Optionally, in the sleep mode, the ambulatory unit 102 can operate in a lower power state such that power is supplied only to components necessary to "wake-up" the ambulatory unit 102. For example, the telemetry circuit 112 can optionally be configured to send a message to the ambulatory unit 102 to initiate the wake mode. The wake mode-sleep mode cycle can define the duty cycle sequence.

Alternatively or additionally, the ambulatory unit 102 can be configured to implement an intra-sample duty cycle, which can be provided to decrease power requirements of the ambulatory unit 102. The intra-sample duty cycle can be reduced to minimize transmission power of the ambulatory unit 102. The intra-sample duty cycle can optionally be the amount of time the ambulatory unit 102 communicates with/transmits data to the base unit 104 during its wake mode. The intra-sample duty cycle can be optimized for the Q of the sensor (e.g., the implanted MEMS-based sensor) and/or the apparent power of the return signals received from the sensor. For example, the ambulatory unit 102 can optionally optimize the amount of time it communicates with/transmits to the base unit 104. The ambulatory unit 102 can optionally be configured to monitor the amplitude of the return signals received from the sensor and reduce the amount of transmission time (e.g., on-time) while the amplitude of the return signal is below a specified threshold. The specified threshold can correspond to a minimum signal to noise ratio. The ambulatory unit 102 can be configured to reduce transmission time when the signal to noise ratio of the return signal is low because useful data might not be recovered due to the low return signal strength. Additionally, the ambulatory unit 102 can be configured to monitor the amplitude of the return signals received from the sensor and increase the amount of transmission time (e.g., on-time) while the amplitude of the return signal is above a specified threshold. The base unit 104 can initiate the reading process by accepting the parameter information specific to the patient's sensor, reading parameters (such as length of readings, sample rates, and frequency ranges, etc.) and patient demographic information. The base unit 104 can then communicate the set-up parameters to the ambulatory unit 104, which initiates the reading process. The base unit 104 can also be configured to display the signal strength from the coupled sensor, for example, on the user interface 120. The base unit 104 can optionally be configured to initiate a frequency scan to locate the sensor within a prescribed frequency range if the signal strength is weak. Additionally, the base unit 104 can also be configured to calculate the pressure measured by the sensor given a calibrated pressure sensor during the measurements. The base unit 104 can also be configured to handle data acquisition requests by acquiring several seconds of measured pressure data, which can include systolic, diastolic, pulse, cardiac output and/or mean pressure values for the acquisition period. The base unit 104 can also be configured to store data to memory. Alternatively or additionally, the base unit 104 can also be configured to communicate data such as the wave form and cardiac output, systolic, diastolic, pulse and mean pressure data to a remote computer, for example, a data server of a monitoring system. As discussed above, the base unit 104 network connectable. Optionally, the base unit 104 can be configured to perform the above functions in real-time. Optionally, the base unit 104 can be configured to perform the above functions on a single patient or multiple patients either simultaneously or in succession.

The data from the readings can optionally be accessed and/or analyzed remotely, for instance, through and application accessed through a network (e.g., the Internet) or through an application resident on the base unit 104. The application can allow a user to access data from individual readings or access historical data from individual patients. The application provides the ability to track trends of physiological measurements and associates those trends with events, activity information, other physiological data and medication changes. this data can then be used by a clinician to more effectively treat the patient's disease state.

The ambulatory system can be used to obtain PA hemodynamic readings as part of any of the methods described herein. In certain embodiments, the ambulatory system is used to obtain ambulatory PA hemodynamic readings from a patient (e.g., while the patient is exercising)

Obtaining Cardiovascular Parameters

Cardiovascular parameters can be determined by analysis of the PA pressure waveform to determine the average maximum waveform values for systolic PAP, average minimum waveform values for diastolic PAP, and average of all waveform values for mean PAP.

Heart rate is optionally determined in the following manner: The timing of repetitive relevant hemodynamic events within the cardiac cycle, such as optionally the average time interval between consecutive systolic or diastolic pressure values, is used to determine the average time interval between beats. The average time interval between beats is optionally used to determine the average heart rate as 60 (s/min.)/average time interval between beats (s/beat) to determine the average heart rate in beats per minute.

Cardiac output (CO) is estimated based on the pulmonary arterial pressure waveform using the following approach. For each cardiac cycle, the pulmonary arterial pressure waveform P(t), comprised of an array of consecutive discrete paired pressure (p) and time (t) values, $P(t)=\{(p_1,t_1), (p_2,t2) \ldots \}$, is optionally analyzed to identify the following relevant reference pressure and time points for each beat:

P1,T1 pressure and time at start of systole and end of diastole.

P2,T2 pressure and time at end of the RV incident wave/beginning of reflected wave indicated as first upslope pressure incisura after the systolic upslope dP/dT max or alternatively at the maximum of the pressure beat.

P3,T3 pressure and time at end of systole/end of outflow demarcated by the dicrotic notch/pulmonic valve closure.

Optionally the pressure waveform features associated with the RV incident pressure wave, and time parameters during systole are used to determine a proportional estimation of stroke volume.

The proportional estimate of stroke volume for each beat, can be determined in a variety of ways, including but not limited to the following:

a. P2−P1
b. $\sqrt{P2}$
c. $\sqrt{(P2-P1)}$
d. $\sqrt{(average(P2,P3))}$
e. $\sqrt{P2} \times (T3-T1)$
f. $\sqrt{(P2-P1)} \times (T3-T1)$
g. $\sqrt{(average(P2,P3))} \times (T3-T1)$
h. $\sqrt{P2} \times (T3-T2)$
i. $\sqrt{(P2-P1)} \times (T3-T2)$
j. $\sqrt{(average(P2,P3))} \times (T3-T2)$
k. dP/dT max value between T1 and T2
l. Integration of P(t)−P1, from T1 to T2.
m. Integration of the first derivative of the pressure waveform, dP(t)/dT, from T1 to T2.
n. Integration of $\sqrt{(P(t)-P1)}$, from T1 to T2.
o. Integration of $\sqrt{dP(t)/dT}$, from T1 to T2.

Alternatively, for estimates which integrate pressure changes over time and which have a downstream reference pressure (P1) (l and n) may be replaced in the equation with a value that gradually increases as the pulmonary vasculature volume increases during filling along the line that is defined by endpoints P1,T1 and P3,T3, according to the equation;

$$P(t)_{[P1,T1 \text{ to } P3,T3]} = P1 + [(P3-P1)/(T3-T1)] \times (t-T1)$$

Accordingly, the proportional estimate of stroke volume can also be performed as follows:

p. Integration of $P(t)-P(t)_{[P1,T1 \text{ to } P3,T3]}$ from T1 to T2.
q. Integration of $\sqrt{(P(t)-P(t)_{[P1,T1 \text{ to } P3,T3]})}$, from T1 to T2.

Alternatively, for estimates that integrate pressure changes or the square root of pressure changes over time (l, n, p, and q), integration over the timeframe from T2 to T3 may also be included, with exclusion of the portion of the waveform which is attributed to the reflected wave. The reflected portion of the waveform is delineated by the line defined by endpoints P2,T2 and P3,T3, defined by the equation;

$$P(t)_{[P2,T2\ to\ P3,T3]} = P2 + [(P3-P2)/(T3-T2)] \times (t-T2)$$

Accordingly, the proportional estimate of stroke volume can also be performed as follows:

r. Integration of P(t)–P1, from T1 to T2 plus integration of $P(t)_{[P2,T2\ to\ P3,T3]}$–P1 from T2 to T3.

s. Integration of $\sqrt{(P(t)-P1)}$, from T1 to T2 plus integration of $\sqrt{(P(t)_{[P2,T2\ to\ P3,T3]}-P1)}$ from T2 to T3.

t. Integration of $P(t)-P(t)_{[P1,T1\ to\ P3,T3]}$ from T1 to T2 plus integration of $P(t)_{[P2,T2\ to\ P3,T3]}-P(t)_{[P1,T1\ to\ P3,T3]}$ from T2 to T3.

u. Integration of $\sqrt{(P(t)-P(t)_{[P1,T1\ to\ P3,T3]})}$, from T1 to T2 plus integration of $\sqrt{(P(t_{[P2,T2\ to\ P3,T3]}-P(t)_{[P1,T1\ to\ P3,T3]})}$ from T2 to T3.

A proportional estimate of stroke volume ($SV_{prop.est}$), is determined as the average of the compiled proportional estimates from at least one cardiac cycle. The duration or number of cardiac cycles for the averaging window can be configured as appropriate to the application. The minimum average length preferably exceeds the length of at least one respiratory cycle in order to average variation attributable to the respiratory cycle.

A proportional estimate of cardiac output is determined by multiplying the average proportional estimate of stroke volume by the measured average heart rate.

An initial reference cardiac output measurement is performed for method calibration, typically during the sensor implantation procedure using a clinically accepted measurement method such as thermodilution, modified Fick, or Fick. During the same measurement session, one or more wireless pulmonary arterial pressure waveform readings are collected. An initial patient specific constant term ($A_i$) is calculated as the ratio of the reference cardiac output measurement and the proportional estimate of cardiac output determined during the same measurement session. This initial patient specific constant term indirectly determines the effects of other relevant parameters such as the RV outflow tract cross sectional area (CSA) and the initial characteristic impedance during the calibration measurements ($Z_{o,i}$); $A_i = CSA \times Z_{o,i}$. This initial patient specific constant term is used as a calibration factor that is multiplied by the proportional estimate of cardiac output to produce the initial estimated cardiac output value; $CO_{est\_Zo,i} = A_o \times SV_{prop.est} \times HR$.

As a corollary to Ohm's law for electrical circuits, the relationship between pressure changes ($\Delta P$) and flow (Q) is governed by flow impedance (Z); $\Delta P(t) = Z(t) \times Q(t)$. Thus, the pressure based proportional estimate of stroke volume and cardiac output is valid only without relevant changes in impedance. This assumption is valid during short term assessments, as would be the case during an initial calibration reading of, for example, 18 s length. However, flow impedance may change over longer timeframes between readings. For this reason, also accounting for changes in impedance between readings is expected to yield improved model performance.

Flow impedance has frequency and non-frequency dependent components.

The frequency dependent components of impedance are primarily associated with reflected, propagated pressure waves which dynamically influence the relationship between pressure and flow. These frequency dependent effects are incorporated into the model through the previously presented use of the first upslope incisura as the T2 timepoint in the initial stroke volume estimate. For example, more prominent reflected pressure waves or faster pressure wave propagation associated with increased pulmonary vascular impedance results in an earlier first upslope incisura, which reduces the proportional estimate of stroke volume. Conversely, less prominent reflected pressure waves or slower pressure wave propagation associated with reduced pulmonary vascular impedance results in a later first upslope incisura, which results in an increased proportional estimate of stroke volume.

In one example, changes in the non-frequency dependent, characteristic impedance after initial calibration are incorporated in order to achieve improved accuracy in the stroke volume and cardiac output estimates without need for recalibration over extended timeframes.

The physiological basis for the non-frequency dependent impedance change estimate, hereafter described as impedance change, $\Delta Z(t)$, is presented as follows. The input stroke volume is a bolus injection that is introduced into the pulmonary vasculature during a minor portion of the total cardiac cycle, indicated by the timeframe from start of systole to the first upslope incisura (T2–T1). Conversely, the outgoing stroke volume leaves the pulmonary vascular through the pulmonary capillaries approximately continuously throughout the entire cardiac cycle. During the relatively short input stroke volume timeframe, a minor portion of the pulmonary vascular blood volume leaves the pulmonary arterial vasculature through the pulmonary capillary beds, approximately (T2–T1)/(Time interval between beats), approximately <10% of the total outgoing stroke volume. Accordingly, changes in resistance have only a minor impact on the characteristic impedance during the short T2–T1 timeframe, and the pulmonary vasculature during the T2–T1 timeframe can be fairly approximated as a closed system, with the major component of characteristic impedance determined by the pulmonary vascular compliance, $\Delta V/\Delta P$.

With increased mean, systolic, or diastolic average pulmonary arterial pressures, the pulmonary arterial wall strain modulus increases, and compliance decreases in a predictable manner, due to the mechanical properties of the pulmonary vessels. (Pasierski T J, CHEST 1993). Based on this relationship, changes in mean, systolic, or diastolic average pulmonary pressures from baseline to a follow-up measurement can be used to infer proportional changes in impedance from baseline values.

The relationship between average pulmonary arterial pressure changes and proportional impedance changes was determined heuristically using data obtained from 54 NYHA Class III Heart Failure patients with 116 follow-up sets of reference cardiac output measurements and wireless pulmonary arterial pressure measurements performed a mean±st. dev. (min., max) of 463±422 (48, 1281) days post implant. The estimated Cardiac Output for follow-up measurements was determined using the initially determined constant term from baseline ($A_i$), which does not account for changing impedance: $CO_{est-Zo,i} = A_o \times SV_{prop.est} \times HR$. The effect of changing impedance was inferred using a scatter plot of the proportional residual error at follow-up, defined as $(CO_{est\_Zo,i} - CO_{ref})/CO_{est\_Zo,i}$, vs. changes in average pulmonary arterial pressure from baseline. There was an observed trend of residual error with respect to mean pressure changes for mean pressure changes in the provided example. The pattern of residual error as a function of mean pulmonary arterial pressure change over the threshold value from baseline to follow-up, $\Delta mPAP$, was characterized using an exponential regression, with constant term coefficient, B=−0.025, by the following equation:

$$\text{Curve fit for proportional residual error at follow-up} = (CO_{est\_Zo} - CO_{ref})/CO_{est\_Zo} = -e^{(B \times \Delta mPAP)} = 1 - e^{(-0.025 \times \Delta mPAP)}$$

$$\text{Predicted residual error} = CO_{est\_Zo} - CO_{ref} = CO_{est\_Zo} \times (1 - e^{(0.025 \times \Delta mPAP)})$$

In order to incorporate the impedance change effect, the predicted residual error is subtracted from $CO_{est-Zo,i}$ to produce a CO estimate with impedance change effects incorporated, $CO_{est\_Z(t)}$.

$$CO_{est\_Z(t)} = CO_{est\_Zo,i} - CO_{est\_Zo,i} \times (1 - e^{(0.025 \times \Delta mPAP)}) = CO_{est\_Zo,i} \times e^{(-0.025 \times \Delta mPAP)}$$

Finally, it should be noted that model coefficients, such as but not limited to the mean pressure threshold value and exponential curve fit coefficient (B), can be used to optimize results based on best fit for a given population or individual patient, using sets of pressure waveform data and CO reference values measured at more than one time with relevant CO change between measurements.

Pulmonary vascular resistance can be calculated from cardiac output (CO) and mean arterial pressure (MAP). For example, PVR is given by:

$$PVR = (MPA - PAW) \times 80/CO$$

wherein MPA is mean pulmonary artery pressure and PAW is pulmonary artery wedge pressure.

Systems

It should be appreciated that the methods and associated signal processing and logical operations described herein can be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the methods and associated signal processing and logical operations discussed herein are not limited to any specific combination of hardware and software. The implementation is a matter of choice dependent on the performance and other requirements of the computing device. Accordingly, the methods and associated signal processing and logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 7:
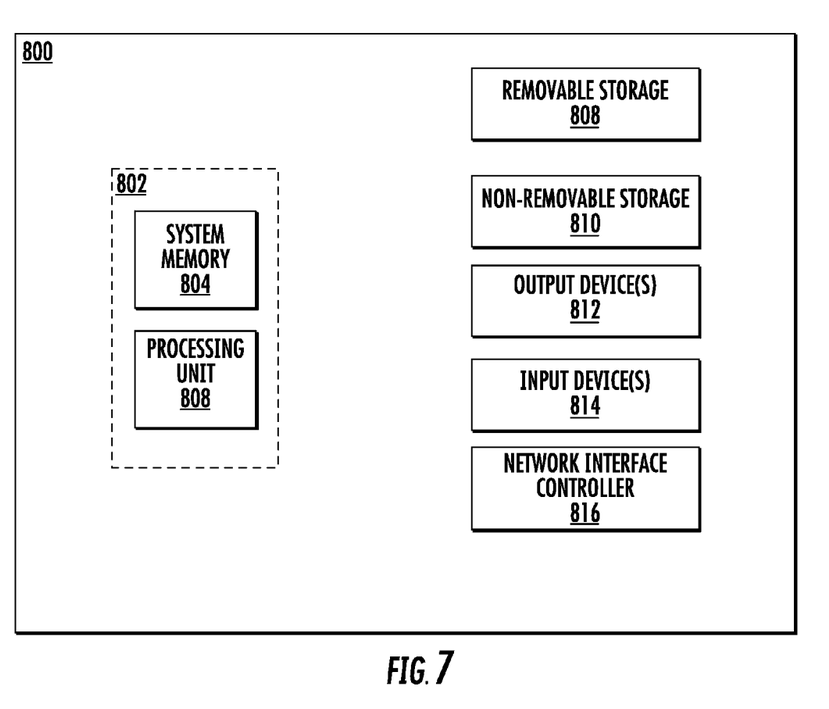
FIG. 7 is an example computing device.

When the methods and associated signal processing and logical operations described herein are implemented in software, the process may execute on any type of computing architecture or platform. For example, referring to FIG. 7, an example computing device upon which embodiments of the invention may be implemented is illustrated. The computing device 800 may include a bus or other communication mechanism for communicating information among various components of the computing device 800. In its most basic configuration, computing device 800 typically includes at least one processing unit 806 and system memory 804. Depending on the exact configuration and type of computing device, system memory 804 may be volatile (such as random access memory (RAM)), non-volatile (such as read-only memory (ROM), flash memory, etc.), or some combination of the two. This most basic configuration is illustrated in FIG. 7 by dashed line 802. The processing unit 806 may be a standard programmable processor that performs arithmetic and logic operations necessary for operation of the computing device 800.

Computing device 800 may have additional features/functionality. For example, computing device 800 may include additional storage such as removable storage 808 and non-removable storage 810 including, but not limited to, magnetic or optical disks or tapes. Computing device 800 may also contain network connection(s) 816 that allow the device to communicate with other devices. Computing device 800 may also have input device(s) 814 such as a keyboard, mouse, touch screen, antenna or other systems configured to communicate with a device configured to obtain a pulmonary artery pressure waveform from a subject, etc. Output device(s) 812 such as a display, speakers, printer, etc. may also be included. The additional devices may be connected to the bus in order to facilitate communication of data among the components of the computing device 800. All these devices are well known in the art and need not be discussed at length here.

The processing unit 806 may be configured to execute program code encoded in tangible, computer-readable media. Computer-readable media refers to any media that is capable of providing data that causes the computing device 800 (i.e., a machine) to operate in a particular fashion. Various computer-readable media may be utilized to provide instructions to the processing unit 806 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 806 may execute program code stored in the system memory 804. For example, the bus may carry data to the system memory 804, from which the processing unit 806 receives and executes instructions. The data received by the system memory 804 may optionally be stored on the removable storage 808 or the non-removable storage 810 before or after execution by the processing unit 806.

Computing device 800 typically includes a variety of computer-readable media. Computer-readable media can be any available media that can be accessed by device 800 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 804, removable storage 808, and non-removable storage 810 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media may be part of computing device 800.

It should be understood that the various techniques described herein may be implemented in connection with hardware or software or, where appropriate, with a combination thereof. Thus, the methods, systems, and associated signal processing of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Also provided are systems for practicing the methods described herein, including systems for evaluating the progression or improvement of cardiovascular condition in a subject being administered a treatment regimen that includes a PDE-5 inhibitor, or predicting an outcome in a subject being administered a treatment regimen that includes PDE-5 inhibitor. Example systems can comprise an implantable pressure sensor (e.g., a pressure sensor implanted in the pulmonary artery of a subject) configured to obtain a pulmonary artery pressure waveform; a processor; and a memory operably coupled to the processor. The memory can include computer-executable instructions stored thereon that, when executed by the processor, cause the processor to receive the one or more PA hemodynamic readings obtained from the implantable pressure sensor; process the PA hemodynamic waveform to obtain a cardiovascular parameter; compare the cardiovascular parameter to a standard; and provide an output based on the comparison of the cardiovascular parameter to the standard.

Example outputs can include indicators or predictors of improvement or worsening of the cardiovascular condition in the subject (e.g., probabilities, scores, subject status indicators, trend values for cardiovascular parameters such as PAP, CO, PVR and/or TPR, graphs plotting values for PAP, CO, PVR and/or TPR, etc.), instructions for treatment (e.g., instructions or indicators to maintain the treatment regimen that includes a PDE-5 inhibitor, instructions to alter the treatment regimen, such as instructions to modify the administration protocol of the PDE-5 inhibitor, instructions to discontinue use of the PDE-5 inhibitor, instructions to administer an alternative therapeutic agent or regimen, etc.) or combinations thereof.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

Example 1

Impact of a Wireless Implanted Pulmonary Artery Pressure Monitoring System in Heart Failure Patients with Pulmonary Hypertension (PH)

The presence of high pulmonary artery pressures are associated with PH exacerbations. A retrospective analysis was performed to evaluate if PA hemodynamic monitoring and therapy reduced PAP in patients with a medical history of HF.

The CHAMPION trial enrolled 537 patients with NYHA class III HF who were followed for an average of 180 days. The patients were divided into two subgroups: Subgroup I: HF patients with optimal pharmacologic therapy (OPT); Subgroup II: clinicians used PA hemodynamic data to guide therapy decisions including the administration of PDE-5 inhibitors in addition to standard of care versus standard of care alone in the control group. Each subgroup was further divided into two sets: Set 1: Mean PAP<25; Set 2: Mean PAP≥25.

Reductions in PAP were analyzed using an area under the curve (AUC) methodology. Overall, treatment in Subgroup I had an average AUC reduction of 564.6 mmHg days in Set 1 and a reduction of 60.4 mmHg days in Set 2. In subgroup I, treatment had an average reduction of 126.3 mmHg days in Set 1 and an increase of 122 mmHg days in Set 2.

Overall, HF OPT patients with HF experience high PAP but have pronounced benefit from PA hemodynamic monitoring in combination with treatment with PDE-5 inhibitors. See Table 1.

TABLE 1

Benefits for HF Patients From PAP-Guided Medical Treatment

| Baseline Mean PA Pressure (mm Hg) | Class III HF OPT 180 Day AUC (mm Hg days) | N | Class III HF OPT + PDE-5 inhibitor 180 Day AUC (mm Hg days) | N | p-value |
|---|---|---|---|---|---|
| Any | −34.8 | 499 | −392.1 | 38 | 0.267 |
| <25 | 122 | 184 | −60.4 | 13 | 0.565 |
| ≥25 | −126.3 | 315 | −564.6 | 25 | 0.477 |

Example 2

Figure 1:
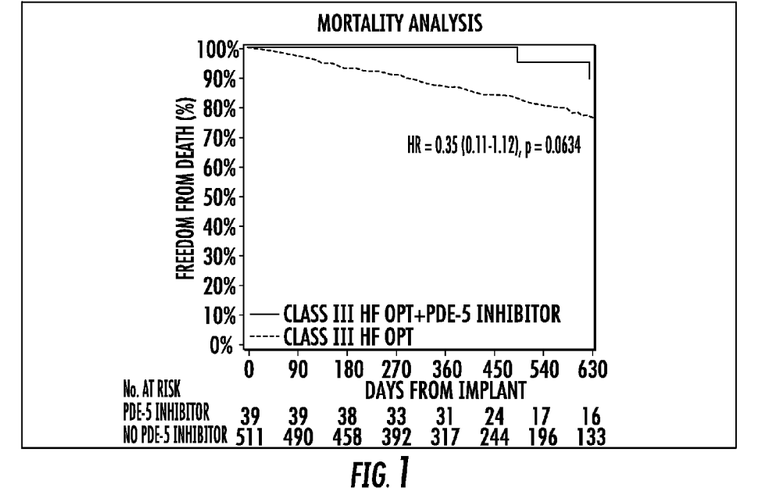
FIG. 1 is a graph showing a mortality analysis of subjects having been administered a PDE-5 inhibitor.
Figure 2:
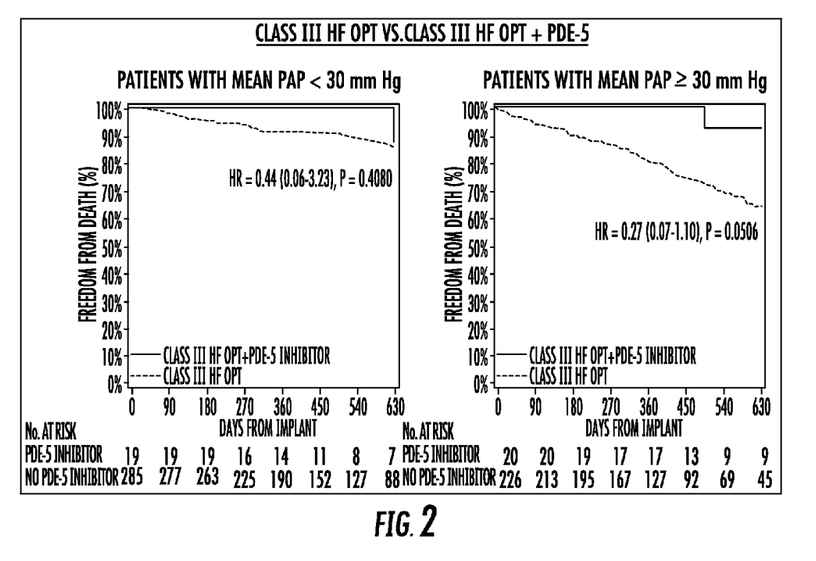
FIG. 2 are graphs showing mortality results in subjects having been administered a PDE-5 inhibitor at different PAP levels. These graphs show elevated mortality rates for PH patients with elevated mean PAP.
Figure 3:
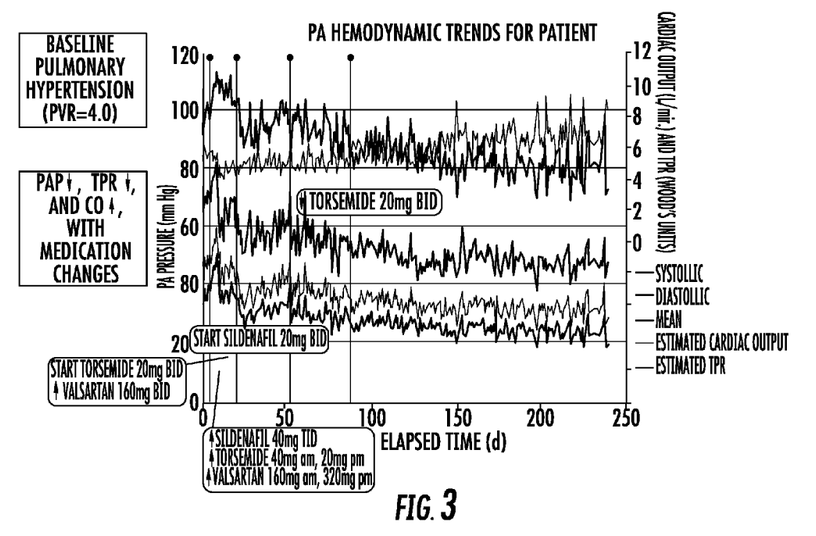
FIG. 3 are graphs showing PA hemodynamic trends.

Hemodynamic Parameters for Evaluation and Monitoring of PAH Using an Implantable Pressure Sensor FIG. 3 shows use of the implantable sensors described herein to determine changes in CO, TPR and PAP after medication revisions in subjects having PH. As shown, the estimated CO was shown to rise after medication revision, while the TPR and mPAP were reduced. The data show the progression of PH in subject following treatment. The data show trends in mPAP, CO and TPR in a subject with PAH. The data further show the combined use of mPAP, CO and TPR trends in monitoring a subject having PH prior and subsequent to administration of a treatment to the subject.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a subject having a cardiovascular condition, comprising:
    (a) administering to the subject a treatment regimen that includes a PDE-5 inhibitor, wherein the PDE-5 inhibitor is selected from tadalafil or sildenafil;
    (b) obtaining one or more pulmonary arterial (PA) hemodynamic readings from the subject using an implantable pressure sensor, wherein the PA hemodynamic readings comprise a PA hemodynamic waveform;
    (c) processing the PA hemodynamic waveform using the processor of a computing device to obtain a cardiovascular parameter, wherein the cardiovascular parameter is selected from the group consisting of pulmonary arterial pressure (PAP), cardiac output (CO), peripheral vascular resistance (PVR), total peripheral resistance (TPR), heart rate, respiratory rate, dicrotic notch information, or combinations thereof;
    (d) comparing the cardiovascular parameter obtained from the subject to a standard to determine the efficacy of the treatment regimen for the treatment of the cardiovascular condition in the subject; and
    (e) maintaining or altering the treatment regimen administered to the subject in view of the indicated efficacy of the treatment regimen for the treatment of the cardiovascular condition in the subject.

2. The method of claim 1, wherein the cardiovascular condition comprises pulmonary hypertension.

3. The method of claim 2, wherein the pulmonary hypertension is associated with left heart disease.

4. The method of claim 2, wherein the pulmonary hypertension is associated with right heart disease.

5. The method of claim 1, wherein the standard comprises a cardiovascular parameter previously determined from the subject.

6. The method of claim 5, wherein the standard comprises a plurality of cardiovascular parameters previously determined from the subject.

7. The method of claim 5, wherein the standard comprises a trend in a cardiovascular parameter in the subject.

8. The method of claim 1, wherein the standard comprises a clinically relevant target cardiovascular parameter for the subject.

9. The method of claim 1, wherein the standard comprises a composite of cardiovascular parameters previously determined from a plurality of subjects.

10. The method of claim 1, wherein the one or more PA hemodynamic readings are remotely obtained.

11. The method of claim 1, wherein the one or more PA hemodynamic readings include ambulatory PA hemodynamic readings.

12. The method of claim 1, wherein the implantable pressure sensor is implanted in a pulmonary artery.

13. The method of claim 1, wherein the implantable pressure sensor lacks percutaneous connections.

14. The method of claim 1, wherein the implantable pressure sensor is energized from an external source.

15. The method of claim 1, wherein the implantable pressure sensor is a passive sensor energized to return pressure readings by an electromagnetic field.

16. The method of claim 1, wherein at least one PA hemodynamic reading is obtained while the subject is exercising.

17. The method of claim 1, wherein at least one PA hemodynamic reading is taken while the subject is asleep.

18. The method of claim 1, wherein the one or more PA hemodynamic readings comprises a high-fidelity PA hemodynamic waveform.

19. The method of claim 1, wherein the cardiovascular parameter is selected from the group consisting of PAP, CO, PVR, TPR, and combinations thereof.

20. The method of claim 1, wherein a decrease in PAP compared to the standard, an increase in CO compared to the standard, a decrease in PVR compared to the standard, or a decrease in TPR compared to the standard indicates efficacy of the treatment regimen for the treatment of the cardiovascular condition in the subject.

21. The method of claim 20, further comprising maintaining the treatment regimen administered to the subject.

22. The method of claim 1, wherein an increase in PAP compared to the standard, a decrease in CO compared to the standard, an increase in PVR compared to the standard, or an increase in TPR compared to the standard indicates substandard efficacy of the treatment regimen for the treatment of the cardiovascular condition in the subject.

23. The method of claim 22, further comprising altering the treatment regimen administered to the subject.

24. The method of claim 23, wherein altering the treatment regimen is selected from the group consisting of modifying the administration protocol of the PDE-5 inhibitor, discontinuing use of the PDE-5 inhibitor, administering an alternative therapeutic agent or regimen, or combinations thereof.

* * * * *